United States Patent
Jakobi (10) Patent No.: US 12,420,078 B2
(45) Date of Patent: Sep. 23, 2025

(54) PERISTALTIC PUMP

(71) Applicant: B. Braun Avitum AG, Melsungen (DE)

(72) Inventor: Marco Jakobi, Uder (DE)

(73) Assignee: B. Braun Avitum AG, Melsungen (DE)

( * ) Notice: Subject to any disclaimer, the term of this patent is extended or adjusted under 35 U.S.C. 154(b) by 0 days.

(21) Appl. No.: 18/732,605

(22) Filed: Jun. 3, 2024

(65) Prior Publication Data
US 2024/0408375 A1    Dec. 12, 2024

(30) Foreign Application Priority Data
Jun. 7, 2023 (DE) .............. 10 2023 115 075.8

(51) Int. Cl.
*A61M 60/20* (2021.01)
*A61M 60/279* (2021.01)
*F04B 43/12* (2006.01)

(52) U.S. Cl.
CPC ....... *A61M 60/279* (2021.01); *F04B 43/1261* (2013.01)

(58) Field of Classification Search
CPC ......... A61M 60/279; F04B 9/00; F04B 53/16; F04B 43/1253; F04B 53/22; F04B 43/1261
See application file for complete search history.

(56) References Cited

U.S. PATENT DOCUMENTS 5,492,455 A * 2/1996 Durham .................. B67D 1/10
                                                    417/313
9,200,628 B2 * 12/2015 Zupp .................. F04B 43/1253
(Continued)

FOREIGN PATENT DOCUMENTS

DE        9409496 U1      6/1995
DE    102010043886 A1     5/2012
(Continued)

OTHER PUBLICATIONS

Search Report received in European Application No. 24179514.5-1004 dated Sep. 18, 2024, with translation, 9 pages.
(Continued)

*Primary Examiner* — Shafiq Mian
(74) *Attorney, Agent, or Firm* — Christopher A. Rothe; CM Law (57) ABSTRACT

A peristaltic pump for conveying fluid in an apparatus for extracorporeal blood treatment includes a pump housing that accommodates a rotor. The rotor includes squeezing elements offset against each other in the circumferential direction. The pump housing includes a support surface extending in a curved shape around the rotor's axis. The support surface is radially spaced from the rotor and arranged to support a tube segment radially inserted between the rotor and the support surface. The rotor is driven by a rotor shaft, the rotary movement of which can be transmitted to a rotor base body via a freewheel press-fitted into a toothed driver sleeve. The freewheel has bearing positions for the rotor base body on both sides of the freewheel. To ensure coaxiality between the freewheel and the bearing support of the rotor base body, the bearing positions are defined by the geometry of the finished driver sleeve.

11 Claims, 5 Drawing Sheets

(56) References Cited

U.S. PATENT DOCUMENTS

| | | | |
|---|---|---|---|
| 9,717,890 B2 | 8/2017 | Holper et al. | |
| 2017/0096665 A1* | 4/2017 | Melquist | C12Y 304/21 |
| 2017/0096995 A1* | 4/2017 | Imai | F04B 43/12 |
| 2018/0245578 A1* | 8/2018 | Winking | F04B 43/1253 |
| 2018/0266410 A1* | 9/2018 | Oude Vrielink | F04B 43/1261 |

FOREIGN PATENT DOCUMENTS

| | | |
|---|---|---|
| DE | 102017103857 A1 | 8/2018 |
| EP | 1749549 B1 | 2/2007 |

OTHER PUBLICATIONS

Search Report received in German Application No. 10 2023 115 075.8 dated Mar. 11, 2024, with translation, 10 pages.

\* cited by examiner

PERISTALTIC PUMP

CROSS-REFERENCE TO RELATED APPLICATION

This application claims priority under 35 U.S.C. § 119 to German Application No. 10 2023 115 075.8, filed on Jun. 7, 2023, the content of which is incorporated by reference herein in its entirety.

FIELD

The present disclosure relates to a peristaltic pump, i.e. a positive-displacement pump, in which the fluid to be conveyed is pressed through a tube by external mechanical deformation of said tube. Pumps of this type are frequently used to convey fluid, specifically blood, in an apparatus for extracorporeal blood treatment, specifically a dialysis machine. The fluid is conveyed by means of the peristaltic pump from a low-pressure side to a high-pressure side, wherein an elastically deformable fluid line arranged between the low-pressure side and the high-pressure side in the form of a tube segment referred to as pump segment is deformed, and specifically squeezed, between a support surface of a pump bed and a rotor rotating relative to the latter and having at least two squeeze elements.

BACKGROUND

Generic peristaltic pumps are available on the market in various configurations. In a pump manufactured e.g. by the applicant of the document EP 1 749 549 B1, whose structure can be taken from the schematic section view according to FIG. 8, the torque is transmitted by a drive shaft 310 with the axis A with the aid of a freewheel 320 and a knurled sleeve 330. A rotor base body 340 is supported via a small plain bearing position 350 at the free end of the drive shaft on the latter, wherein the plain bearing position 350 is located axially offset against the knurled sleeve 330 which extends only to the middle of the rotor base body 340. The plain bearing 350 is thus integrated in the base body 340 of the rotor.

Figure 8:
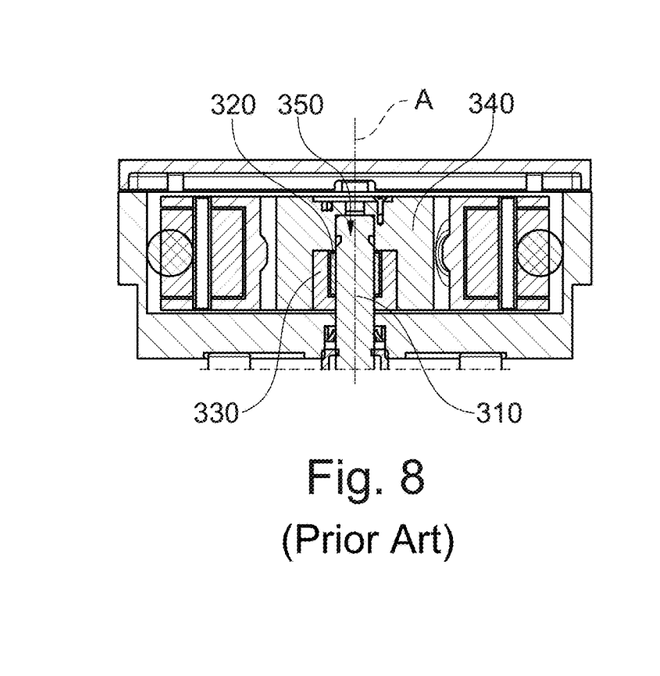
FIG. 8 shows a schematic section view of a pump according to the state of the art.

In order to ensure the coaxiality between the freewheel 320 and the bearing 350, high requirements have to be made to the accuracy of the knurled sleeve and the base body. As, furthermore, only a small one-sided bearing support of the rotor base body 340 is provided, radial forces and tilting moments can be absorbed to a limited extent only. Although the knurled sleeve is knurled over the entire height, due to its small axial extension height and the assembly in the axially outer area of the rotor base body 340, however, the torque to be transmitted is introduced to the lower area only and therefore remains relatively limited.

Figure 9:
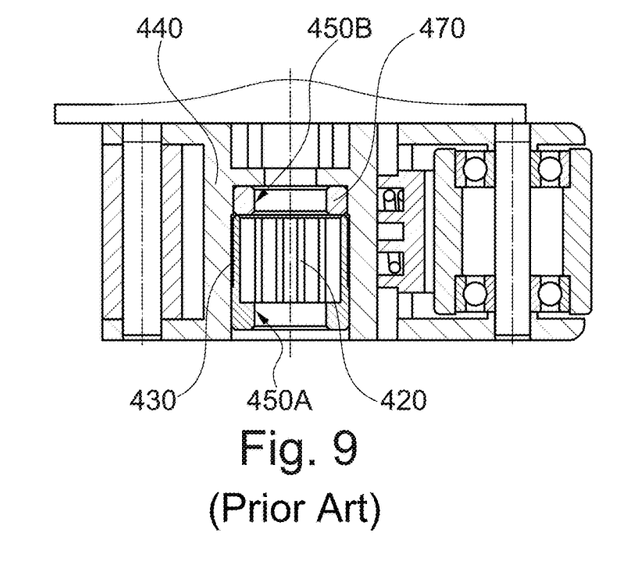
FIG. 9 shows a schematic partial section of a known rotor base body with a press-fitted freewheel.
Figure 10:
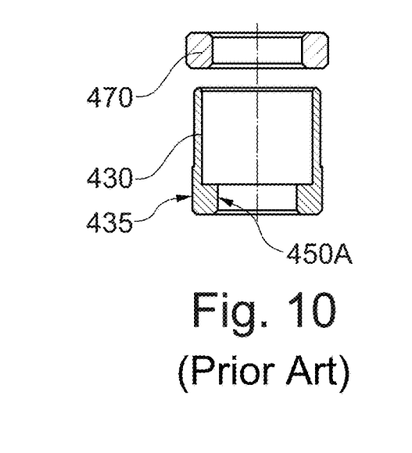
FIG. 10 shows a section view of a knurled sleeve and a bearing ring used in the pump according to FIG. 9.

Another generic peristaltic pump comprising the features of the preamble of claim 1 is known which is has a structure as shown in FIGS. 9 and 10. FIG. 9 illustrates a partial section of a rotor base body with a press-fitted freewheel, while FIG. 10 illustrates a section view of a knurled sleeve used therewith and a bearing ring. In said peristaltic pump, the torque is transmitted from the drive shaft to the rotor base body 440 equally by a freewheel 420 that is press-fitted into a knurled sleeve 430. The knurled sleeve 430 in turn is press-fitted into a cylindrical recess of the rotor base body 440. The freewheel is provided to enable the pump segment to be manually threaded in and out and the manual blood return without any lock having to be opened. Sleeve freewheels without roller bearings are friction couplings and can only transmit torques. Since they cannot absorb any radial forces or tilting moments, the bearing support of the rotor base body 440 has two plain bearing positions which are denoted with the reference numerals 450A and 450B. The one edge-side bearing position 450A is integrated in the knurled sleeve 430 below the freewheel, as shown in FIG. 9. Radially outside the bearing position 450A, viz. where the wall thickness of the knurled sleeve 430 is larger, the knurl 435 is arranged. The second bearing position 450B is formed by a separate bearing ring 470 which is press-fitted, according to FIG. 8, above the knurled sleeve 430 into a stepped bore of the rotor base body 440. Said structure requires high manufacturing accuracies not only for the parts of knurled sleeve 430 and bearing ring 470, but also for the mount in the rotor base body 440, so as to ensure the coaxiality between the freewheel 420 and the bearing 450A, B. In addition, it is clear that also with this structure the transmittable torque remains limited, as it can be introduced only via the knurl 435 arranged at the edge.

SUMMARY

The object underlying the present disclosure is to provide a peristaltic pump in which the coaxiality between the freewheel and the bearing support is ensured with less manufacturing effort, while a non-tilting bearing support of the rotor base body is maintained.

In the newly designed peristaltic pump, there are still provided two plain bearing positions to absorb radial forces and tilting moments. Said plain bearing positions are designed, however, so that they are defined on both sides of the freewheel by the geometry of the finished driver sleeve. This results in the special advantage that the high requirements made to the accurate manufacture are restricted to the knurled sleeve and a bearing ring possibly received therein so as to ensure the coaxiality between the freewheel and the bearing support. The rotor base body, on the other hand, can be manufactured with larger tolerances, resulting in a significantly reduced manufacturing effort. In addition, this configuration offers the option to minimize the space for designing the bearing positions and the torque transmission.

According to an advantageous configuration, one bearing position is formed by an edge-side cylindrical inner surface portion of the driver sleeve and the other bearing position is formed by a bearing ring inserted with press-fit into the driver sleeve. In this way, the bearing points can be arranged at a large axial distance, which allows to absorb the radial forces and tilting moments even by components such as, e.g., a drive shaft which require reduced space.

The manufacture is further simplified, while simultaneously ensuring a highly precise coaxial alignment of the freewheel and the bearing support, when the driver sleeve has a continuous, i.e. common, fitting surface for the press-fitted freewheel and the bearing ring.

Another advantageous configuration consists in designing the driver sleeve on the outside at least with a toothing section that can be pressed into a centric recess of the rotor base body designed with a draft angle for manufacturing a rotationally fixed positive or form fit connection. In this way, the rotor base body can be designed as an injection molded part, wherein the recess in the rotor base body does not require any more finishing work.

If two axially spaced toothing sections which are located radially outside the bearing points or positions are provided, the torque can be transmitted particularly uniformly to the rotor base body, thus allowing the transmissible torque to be further increased while the installation size is small.

The arrangement is particularly advantageous in connection with the configuration of the rotor base body as a casting, if the toothing sections have diameters of different sizes and the centric recess of the rotor base body includes plural sections having different diameters and draft angles. This meets the requirements made to a configuration appropriate for injection molding. Moreover, in this way, press-fitting of the knurled sleeve can be facilitated and the required draft angle can be optimized.

BRIEF DESCRIPTION OF THE DRAWINGS

In the following, embodiments of the present disclosure shall be illustrated in detail by way of schematic drawings, wherein.

DETAILED DESCRIPTION

Figure 1:
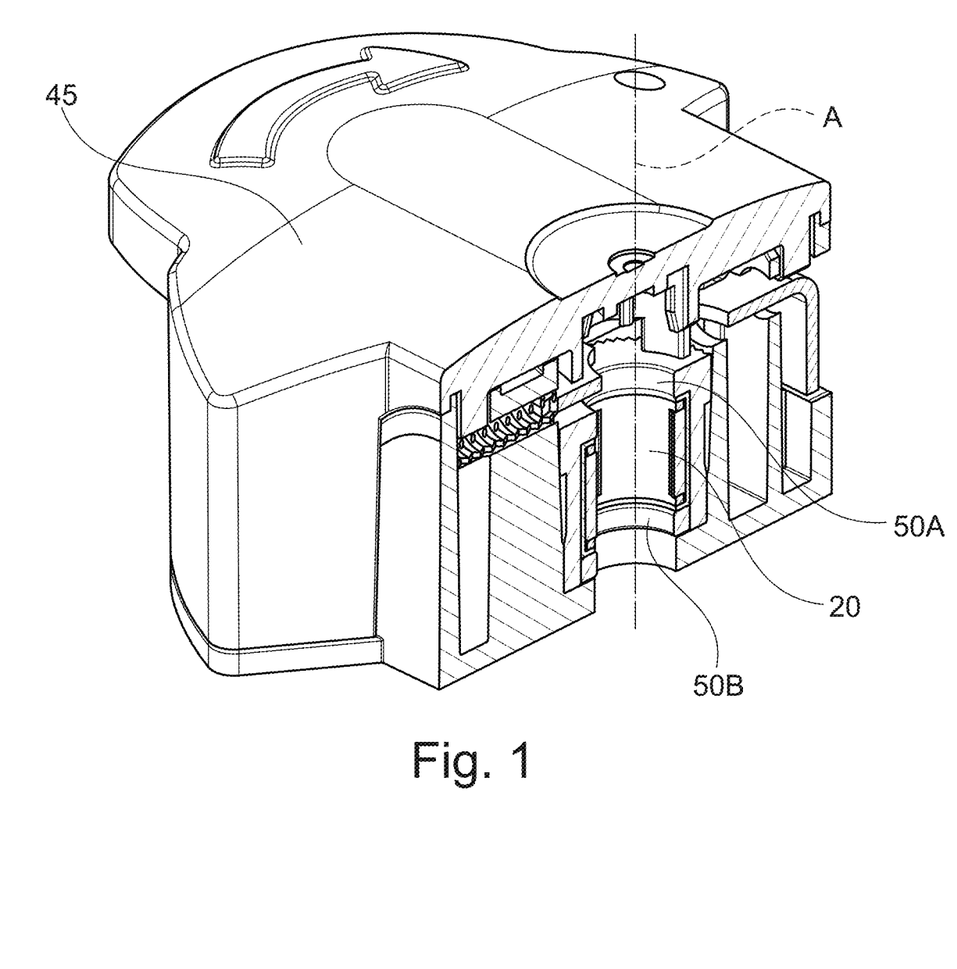
FIG. 1 shows a perspective central section view of a rotor of a peristaltic pump according to a first embodiment.

FIG. 1 illustrates the central section view of a rotor 10 of a peristaltic pump that can be used in an apparatus for extracorporeal blood treatment, and specifically in a dialysis machine. The peristaltic pump includes a pump housing not shown in detail in which a rotor rotatable about a rotor axis A and having at least two squeezing elements 46 offset against each other in the circumferential direction (see FIG. 5) is accommodated, said squeezing elements being constituted by rollers in the embodiment according to FIGS. 1 to 6. The pump housing has a support surface extending in curved shape around the rotor axis A and being radially spaced apart from the rotor which is arranged to support a tube segment that can be radially inserted between the rotor and the support surface.

Figure 2:
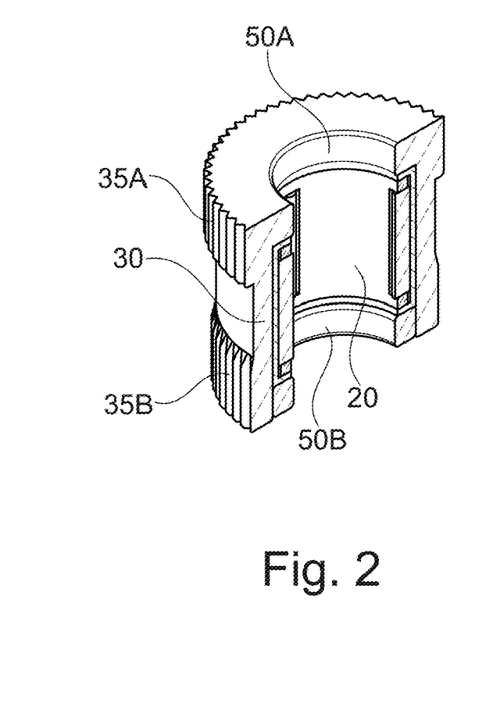
FIG. 2 shows a perspective section view of a knurled sleeve with a press-fitted freewheel used in the peristaltic pump according to FIG. 1.

In the shown embodiment, the peristaltic pump has a drive shaft (not shown) with an axis of rotation A by which a rotor base body 40 supporting a rotor cover 45 can be driven. The torque of the drive shaft is transmitted to the rotor base body 40 via a sleeve freewheel 20 (see FIGS. 2 and 3). For this purpose, a toothed driver sleeve hereinafter referred to as knurled sleeve 30 (see FIG. 2) is provided into which the sleeve freewheel 20 including freewheel rolling bodies 25 is press-fitted. The freewheel is provided to allow for manually threading a pump segment in and out and for the manual blood return without any lock having to be opened. The sleeve freewheel is a freewheel without a roller bearing and, thus, a type of friction coupling by which only moments can be transmitted.

Figure 5:
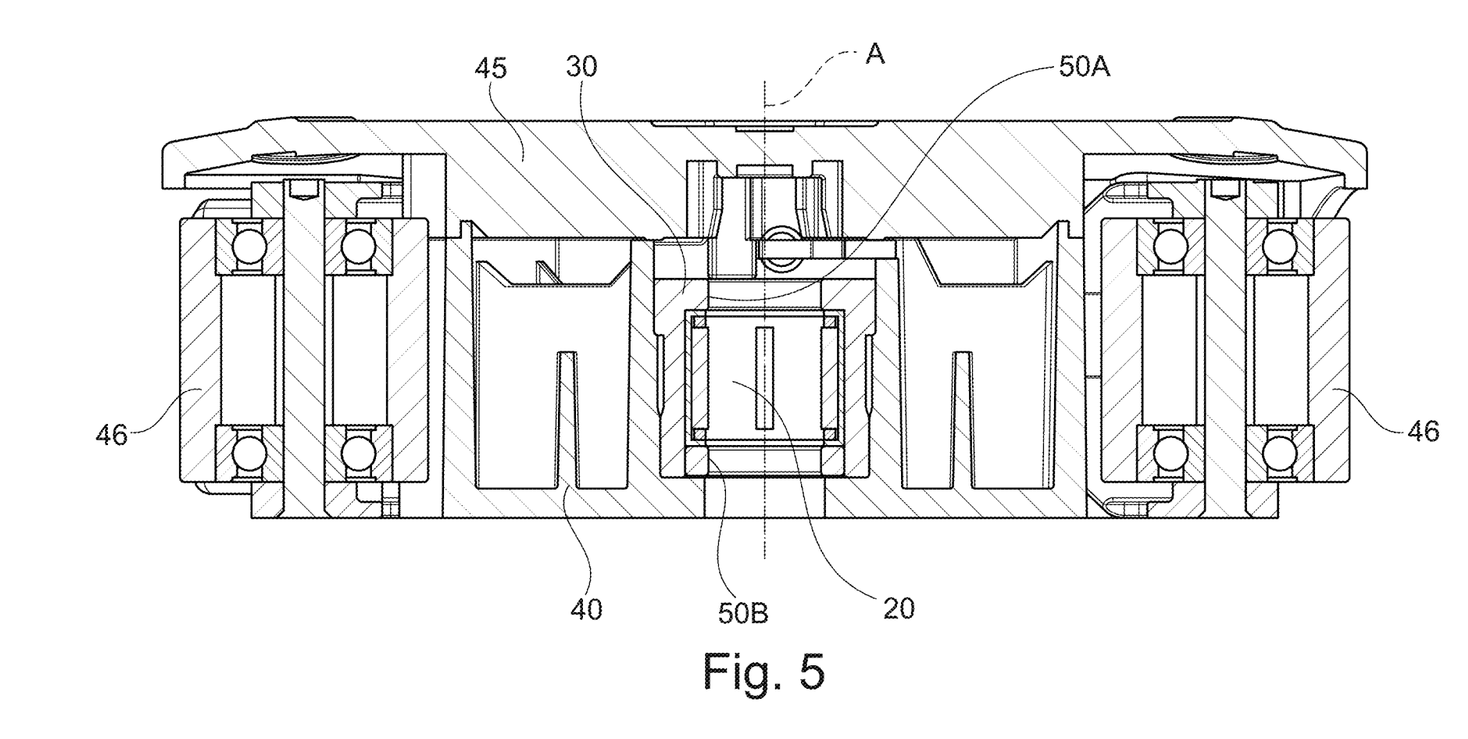
FIG. 5 shows the section view of the rotor of the peristaltic pump.
Figure 6:
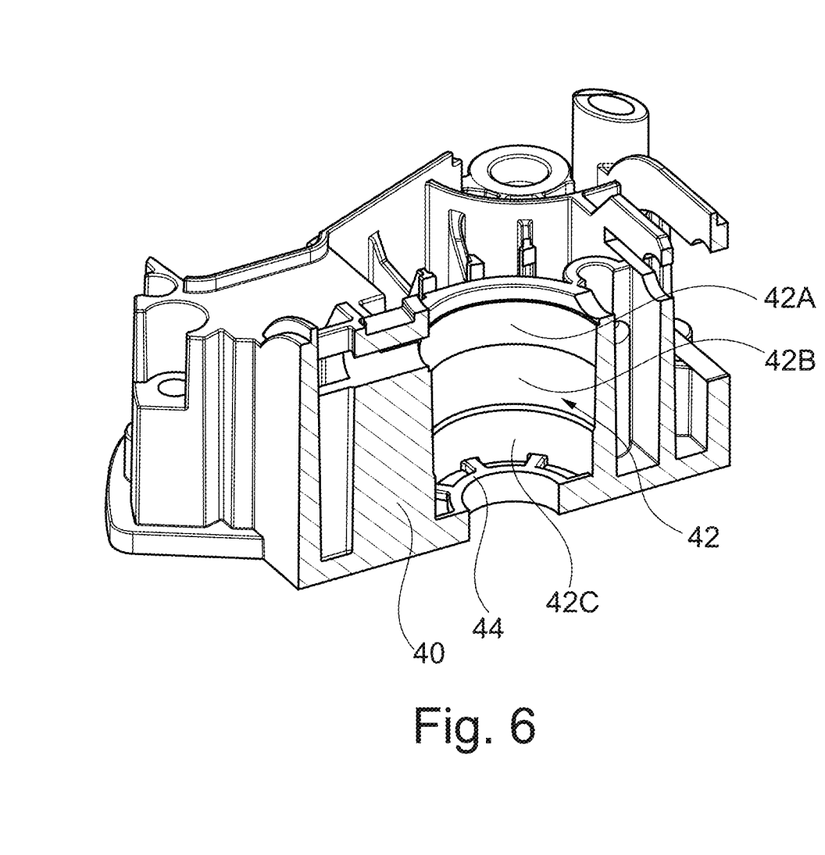
FIG. 6 shows a perspective central section view of the rotor base body of the peristaltic pump shown in FIGS. 1 to 5.

The knurled sleeve 30 in turn is press-fitted—as can be seen from FIGS. 1 and 5—into the base body 40 of the rotor, namely into a centric mount 42 including a stop shoulder 44 (FIG. 6). For a rotationally fixed connection to the rotor base body 40, the knurled sleeve 30 includes two straight knurls 35A and 35B each of which is formed at the axial end sections of the knurled sleeve 30. In the shown embodiment, the knurls 35A have different outer diameters D35A and D35B. A smooth recess or turned groove 36 is located between the knurls 35A and 35B.

For absorbing radial forces and tilting moments, slide or plain bearings—named bearing positions 50A and 50B are provided on both sides of the sleeve freewheel 20. The plain bearing position 50A is formed by a cylindrical annular surface of an end-side inner shoulder 37 of the knurled sleeve 30. The other plain bearing position 50B is formed by the bearing surface of a bearing ring 39 press-fitted into the knurled sleeve 30. In this way, the plain bearing positions 50A and 50B and their position relative to each other on both sides of the freewheel 20 are defined by the geometry of the finished knurled sleeve 30. Since the freewheel 20 is press-fitted into a fitting surface of the knurled sleeve 30 anyway, the required coaxiality between the bearing points or positions 50A, 50B and the freewheel 20 can be ensured solely by the manufacture of the knurled sleeve 30. In other words, solely the manufacturing accuracy of the knurled sleeve 30 and the bearing ring 39 defines the coaxiality of the freewheel 20 and the bearing of the rotor base body 40 so that the rotor base body 40 can be manufactured with larger tolerances, which results in a significantly reduced manufacturing effort. In addition, this concept offers the option to minimize the available space for the configuration of the bearing positions or points and the torque transmission.

Figure 3:
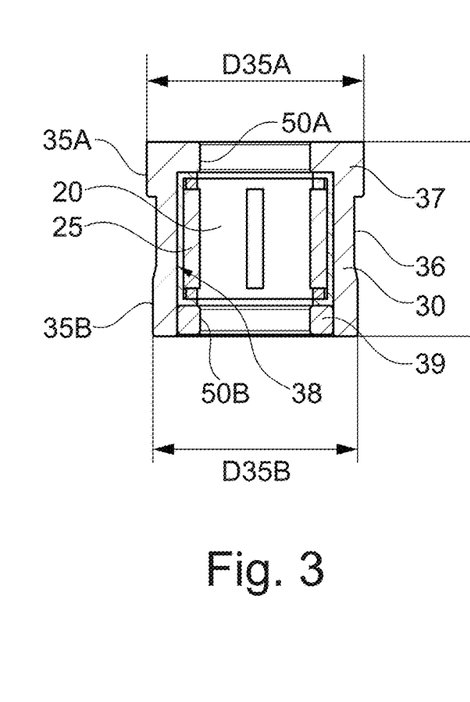
FIG. 3 shows the section view of the knurled sleeve with a press-fitted freewheel according to FIG. 2.

It is evident from FIG. 3 that the bearing ring 39 is press-fitted into a cylindrical joint fitting area 38 which simultaneously forms the joint area for the sleeve freewheel 20. This allows to further simplify manufacture.

Figure 4:
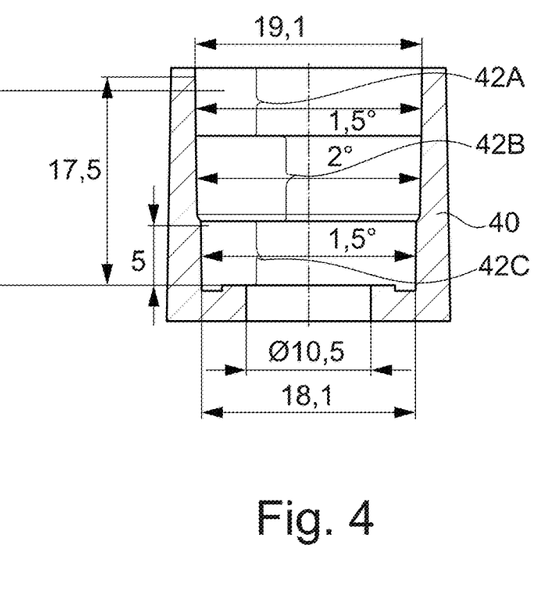
FIG. 4 shows, in an enlarged scale, the section view of a mount in the rotor base body for the knurled sleeve according to FIGS. 2 and 3.

Since the rotor base body 40 can be manufactured with larger tolerances due to the above-described arrangement of the sleeve freewheel 20 and the plain bearing positions 50A and 50B, it can be designed as an injection molded part, such as a metallic or preferably glass-fiber reinforced plastic injection molding without finishing. The configuration of the knurls 35A and 35B accommodates this as follows:

Since the knurl 35A has a larger outer diameter than the knurl 35B, the mount 42 for the knurled sleeve 30 in the base body can be divided—as shown in FIG. 4—into plural sections 42A to 42C having different diameters and draft angles. The sections 42A and 42C are slightly conical, such as at a cone angle of 1.5°. Said sections 42A and 42C are adjusted, regarding their diameter and regarding their axial extension, to the associated knurls 35A and 35B so that, when the knurled sleeve 30 with its straight knurls 35A and 35B is pressed in and a material displacement is resulting, an evenly tight toothing occurs between the knurled sleeve and the rotor base body 40 so that the torque initiated by the rotor shaft can be distributed as uniformly as possible to the rotor base body 40 substantially over the entire construction height thereof. For the form fit or positive connection between the knurled sleeve 30 and the rotor base body 40 is located substantially radially outside the bearing points or positions 50A and 50B. The section 42B located between the sections 42A and 42C is designed as a draft angle having a somewhat larger cone angle of 2°.

In the afore-described embodiment, the arrangement is made such that the knurled sleeve 30 supports the bearing ring 39 on the side where the knurl 35B having the smaller diameter D35B is formed. The bearing point or position 50A facing the rotor cover 45 is formed by the knurled sleeve 30.

Figure 7:
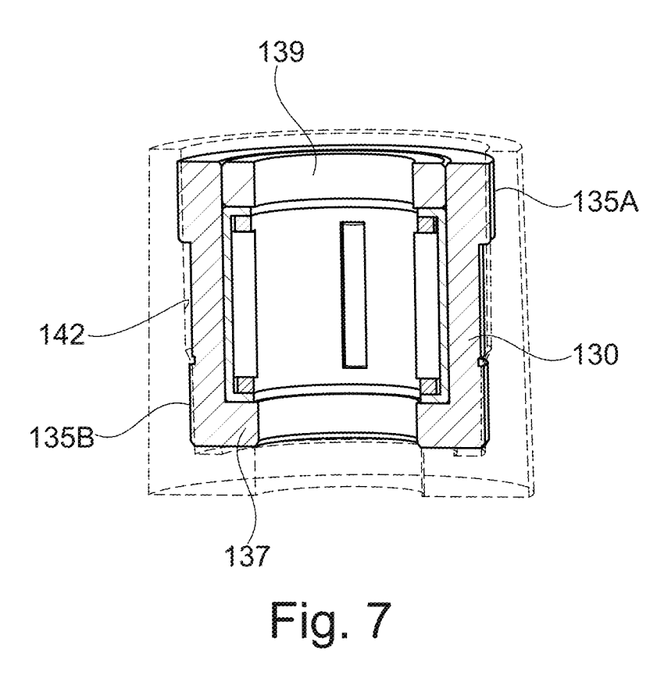
FIG. 7 shows the section view of a modified configuration of a knurled sleeve with a press-fitted freewheel inserted in the rotor base body.

FIG. 7 illustrates a modified configuration of the assembly unit. In this Figure, components corresponding to component parts of the afore-described embodiment are provided with similar reference numerals which are preceded with "1".

In this case, the inner shoulder 137 of the knurled sleeve 130 is formed on the side where the smaller-diameter knurl 135B is configured. The bearing ring 139 is press-fitted on the other side, i.e. radially inside the larger-diameter knurl 135A, into the joint fitting area of the knurled sleeve 130. The mount 142 formed in the rotor base body corresponds to the mount 42 of the embodiment according to FIGS. 1 to 6.

Consequently, the present disclosure provides a peristaltic pump, specifically for conveying fluid in an apparatus for extracorporeal blood treatment, comprising a pump housing in which a rotor rotatable about a rotor axis and having at least two squeezing elements offset against each other in the circumferential direction is accommodated. The pump housing includes a support surface extending in curved shape around the rotor axis and being radially spaced apart from the rotor, the support surface being arranged to support a tube segment that can be radially inserted between the rotor and the support surface. The rotor is driven by means of a rotor shaft the rotary movement of which can be transmitted to a rotor base body via a freewheel press-fitted into a toothed driver sleeve, and a plain bearing position for the base body is provided on both sides of the freewheel. In order to ensure the coaxiality between the freewheel and the non-tilting support of the rotor base body with little manufacturing effort, the plain bearing positions are defined on both sides of the freewheel by the geometry of the finished driver sleeve.

LIST OF REFERENCE NUMERALS

A axis
20 sleeve freewheel
25 freewheel rolling body
30 knurled sleeve
35A, B knurls
36 turned groove (recess)
37 inner shoulder
38 joint fitting area
39 bearing ring
40 rotor base body
42 mount
42A, B, C sections of 42
44 stop shoulder
45 rotor cover
46 squeezing elements
50A, B plain or slide bearing positions
120 freewheel
130 knurled sleeve
135A, B knurls
139 bearing ring
310 drive shaft
320 freewheel
330 knurled sleeve
340 rotor base body
350 bearing position
420 sleeve freewheel
430 knurled sleeve
435 knurl
450A, B plain bearing positions
470 bearing ring

The invention claimed is:

1. A peristaltic pump for conveying fluid in an apparatus for extracorporeal blood treatment, the peristaltic pump comprising a pump housing that accommodates a rotor rotatable about a rotor axis, the rotor including at least two squeezing elements offset against each other in a circumferential direction, the pump housing including a support surface extending in a curved shape around the rotor axis, the support surface being radially spaced apart from the rotor and arranged to support a tube segment radially inserted between the rotor and the support surface, the rotor being driven by a rotor shaft, the peristaltic pump further comprising a freewheel press-fitted into a toothed driver sleeve that is configured to transmit rotary movement of the rotor shaft to a rotor base body, the rotor base body comprising a plain bearing position on each side of the freewheel, the plain bearing positions being defined by a geometry of the toothed driver sleeve, with one of the plain bearing positions comprising a bearing ring.

2. The peristaltic pump according to claim 1, wherein the plain bearing positions comprise a first bearing position and a second bearing position, the first bearing position formed by an edge-side cylindrical inner surface portion of the toothed driver sleeve and the second bearing position formed by the bearing ring.

3. The peristaltic pump according to claim 2, wherein the toothed driver sleeve has a continuous fitting area for the freewheel and the bearing ring.

4. The peristaltic pump according to claim 1, wherein the toothed driver sleeve comprises at least one toothing section that is pressable into a centric recess of the rotor base body to establish a rotationally fixed positive or form fit connection.

5. The peristaltic pump according to claim 4, wherein the at least one toothing section comprises two toothing sections that are axially spaced and located radially outside the plain bearing positions.

6. The peristaltic pump according to claim 5, wherein the two toothing sections have differently sized diameters, and the centric recess of the rotor base body includes sections having different diameters and draft angles.

7. The peristaltic pump according to claim 6, wherein the sections of the centric recess are each conical with a cone opening in a common direction.

8. The peristaltic pump according to claim 7, wherein the sections of the centric recess comprise first sections adapted to receive the two toothing sections and a second section between the first sections, the first sections having first cone angles, and the second section having a second cone angle, each first cone angle being smaller than the second cone angle.

9. The peristaltic pump according to claim 1, wherein the rotor base body is an injection-molded part.

10. The peristaltic pump according to claim 9, wherein the injection-molded part is made of glass-fiber reinforced plastic or light metal.

11. A peristaltic pump for conveying fluid in an apparatus for extracorporeal blood treatment, the peristaltic pump comprising a pump housing that accommodates a rotor rotatable about a rotor axis, the rotor including at least two squeezing elements offset against each other in a circumferential direction, the pump housing including a support surface extending in a curved shape around the rotor axis, the support surface being radially spaced apart from the rotor and arranged to support a tube segment radially inserted between the rotor and the support surface, the rotor being driven by a rotor shaft, the peristaltic pump further comprising a freewheel press-fitted into a toothed driver sleeve that is configured to transmit rotary movement of the rotor shaft to a rotor base body, the rotor base body comprising a plain bearing position on each side of the freewheel, the plain bearing positions being defined by a geometry of the toothed driver sleeve, wherein the plain bearing positions comprise a first bearing position and a second bearing position, the first bearing position formed by an edge-side cylindrical inner surface portion of the toothed driver sleeve and the second bearing position formed by a bearing ring inserted with press-fit into the toothed driver sleeve.

\* \* \* \* \*